United States Patent [19]

Schaerfl, Jr. et al.

[11] Patent Number: 5,516,958
[45] Date of Patent: May 14, 1996

[54] PREPARATION OF ALPHA, OMEGA-DIENE OLIGOMERS AND DERIVATIVES THEREOF

[75] Inventors: Robert A. Schaerfl, Jr.; Ali M. Dadgar, both of Baton Rouge; Carroll W. Lanier, Baker, all of La.

[73] Assignee: Albemarle Corporation, Richmond, Va.

[21] Appl. No.: 166,774

[22] Filed: Dec. 14, 1993

[51] Int. Cl.$^6$ .................................................. C07C 2/08
[52] U.S. Cl. ........................ 585/522; 585/10; 585/12; 585/511
[58] Field of Search ............................. 585/511, 572, 585/520, 522, 10, 12

[56] References Cited

U.S. PATENT DOCUMENTS

| | | | |
|---|---|---|---|
| 3,324,191 | 6/1967 | Wofford | 260/669 |
| 3,351,621 | 11/1967 | Bacskai | 260/88.2 |
| 3,356,754 | 12/1967 | Wofford | 260/669 |
| 3,360,580 | 12/1967 | Mertzweiller et al. | 260/669 |
| 3,472,830 | 10/1969 | Baxter et al. | 260/94.2 |
| 3,624,175 | 11/1971 | Zuech | 260/677 R |
| 4,041,088 | 8/1977 | Bach et al. | 260/668 B |
| 4,049,732 | 9/1977 | Bach et al. | 260/668 B |
| 4,060,492 | 11/1977 | Yasui et al. | 252/59 |
| 4,061,780 | 12/1977 | Yoshida et al. | 424/358 |
| 4,078,010 | 3/1978 | Prillieux et al. | 260/676 R |
| 4,340,705 | 7/1982 | Lal et al. | 526/139 |
| 4,440,965 | 4/1984 | Palmer | 585/12 |
| 4,551,503 | 11/1985 | Lal et al. | 525/332.1 |
| 5,306,856 | 4/1994 | Streck et al. | 585/508 |
| 5,366,658 | 11/1994 | Hoppe et al. | 252/56 S |

FOREIGN PATENT DOCUMENTS

| | | | |
|---|---|---|---|
| 779363 | 2/1968 | Canada | 260/691 |
| 0390492 | 10/1990 | European Pat. Off. | C08F 136/20 |
| 0518021 | 12/1992 | European Pat. Off. | C07C 2/30 |

OTHER PUBLICATIONS

Marvel, et al., "Polymerization of Higher α–Diolefins with Metal Alkyl Coordination Catalysts", J. Am. Chem. Soc., vol. 81, (1959), pp. 4736–4744.
Chemical Abstract, vol. 111, 1989, abstract No. 78655x.
Chemical Abstract, vol. 104, 1986, abstract No. 226170h.
Chemical Abstract, vol. 97, 1982, abstract No. 164341r.
Chemical Abstract, vol. 96, 1982, abstract No. 35923n.
Chemical Abstract, vol. 79, 1973, abstract No. 79272c.
Chemical Abstract, vol. 68, 1968, abstract No. 3340a.

*Primary Examiner*—Ponnathapura Achutamurthy
*Attorney, Agent, or Firm*—Philip M. Pippenger; David M. Bunnell

[57] ABSTRACT

α,ω-Diene oligomers which are useful as synthetic lubricants are prepared by oligomerizing a α,ω-diene using a trialkylaluminum catalyst.

10 Claims, No Drawings

PREPARATION OF ALPHA, OMEGA-DIENE OLIGOMERS AND DERIVATIVES THEREOF

This invention relates generally to diene oligomers and more specifically to linear α,ω-diene oligomers which have reactive vinylidene groups along the backbone of the oligomer chain and which are useful as lubricants and lubricant additives.

Synthetic hydrocarbon lubricants are known in the art. For example, polyalphaolefins (PAO'S) are made by oligomerizing $C_6$ to $C_{20}$ α-olefins. These oligomer fluids are usually hydrogenated to improve their stability to oxidation. The residual internal double bond in each molecule can also be functionalized to form, for example, alkyl phenols, carboxylic acids and esters, alcohols, mercaptans, aldehydes, sulfonates and the like. However, the hindered nature of the double bond can make functionalization difficult, especially with higher oligomers. Also, because only one double bond is available, the ability to form multifunctional molecules is limited.

We have found that substantially straight chain, low molecular weight synthetic fluids can be prepared by oligomerizing α,ω-dienes using an aluminum alkyl catalyst. These oligomers possess a series of vinylidene groups along the backbone of the oligomer chain which are readily available to react so as to permit the easy formation of derivatives of the oligomers.

In one embodiment of the invention the oligomers can be hydrogenated to form a saturated synthetic lubricant which has excellent lubricating properties, including low NOACK volatility and a very high viscosity index.

In accordance with this invention there is provided a process for preparing a substantially linear oligomer of a α,ω-diene which has vinylidene groups along and directly attached to the oligomer chain. The process comprises reacting a α,ω-diene in the presence of an organoaluminum catalyst so as to form said oligomer.

Also provided is a substantially linear oligomer of a $C_5$ to $C_{30}$ α,ω-diene, said oligomer having the structural formula:

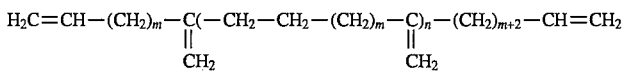

where m is an integer of from 1 to 26 and n is an integer of from 0 to about 100. Preferably, n is an integer of from 0 to about 50.

Also provided is an end-capped α,ω-diene oligomer having the structural formula:

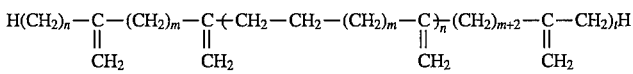

where m is an integer of from 1 to about 26, n is an integer of from 0 to about 100, and s and t are integers of from about 3 to 30 and can be the same or different.

Non-limiting examples of α,ω-dienes for use in the process of the invention, preferably, contain from 5 to 30 carbon atoms in the chain and can be substituted elsewhere than at the double bonds by alkyl, cycloalkyl, aryl or aralkyl groups having from 1 to 30 carbon atoms. Specific α,ω-dienes include 1,4-pentadiene, 1-6-heptadiene, 1,7-octadiene, 1,8-nonadiene, 1,9-decadiene, 1,10-undecadiene, 1,11-dodecadiene, 1,12-tridecadiene, 1,13-tetradecadiene, 1,14-pentadecadiene, 1,15-hexadecadiene, 1,16-heptadecadiene, 1,17-octadecadiene, 1,18-nonadecadiene, 1,19-eicosadiene, and the like including mixtures thereof. By choosing different dienes, the spacing between the vinylidene groups can be selected to provide oligomers whose properties are tailored to specific applications.

Suitable aluminum alkyl compounds for use as catalysts preferably contain two or three alkyl groups, each having from 1 to about 20 carbon atoms. Non-limiting examples of aluminum alkyls include trimethylaluminum, triethylaluminum, tri-n-propylaluminum, tri-n-butylaluminum, triisobutylaluminum, tri-n-hexylaluminum, tri-n-octylaluminum, tri-n-decylaluminum, tri-n-dodecylaluminum, diisobutylaluminum hydride, and the like. The catalysts are used in effective amounts to oligomerize the α,ω-diene. Preferably, mole ratios of catalyst to diene of from about 1:1,000 to 1:10 are used with mole ratios of from about 1:20 to 1:100 being preferred.

The reaction can be carried out neat or in the presence of an inert dry organic solvent. Non-limiting examples of suitable solvents include linear and cyclic aliphatic hydrocarbons containing from about 4 to 20 carbon atoms, such as pentane, isopentane, hexane, cyclohexane, heptane, octane, decane, hexadecane, and the like, and aromatic solvents having from about 6 to 20 carbon atoms such as benzene, toluene, xylene, ethylbenzene, cumene mesitylene, and the like.

The reaction temperatures are chosen to provide oligomerization in a reasonable time without causing side reactions such as isomerization of the vinylidene groups or the formation of deep internal olefins and, preferably, range from about 50° to 200° C. More preferably the temperature ranges from 100° to 140° C. and most preferably from 120° to 125° C. At temperatures above 140° C. the mechanism of internal olefin formation becomes significant. Temperatures of 120° to 125° C. maximize the formation of the desired vinylidene products (90%+) at reasonable reaction times. Reaction pressures preferably range from atmospheric to about 1,000 psig. The oligomers have number average molecular weights $M_n$ ranging from about 150 to 3,000 and, preferably, from about 250 to 1,800.

"End-capping" of the vinyl groups at the end of the oligomer chain is accomplished by adding $C_6$ to $C_{30}$ alpha mono-olefins to the reaction. A vinylidene is formed at the reaction site but the new ends of the polymer are saturated and unreactive. Under relatively mild conditions, the vinylidene groups along the chain do not react. Some of the added alpha-olefins react with themselves to form vinylidene compounds.

Non-limiting examples of alpha-olefins which can be used for end-capping include 1-butene, i-pentene, 1-hexene, 1-octene, 1-decene, 1-dodecene, 1-tetradecene, 1-hexadecene, 1-octadecene, and the like including mixtures thereof. Preferably, amounts of from about 0.05 to 5 moles of alpha-olefin per mole of α,ω-diene are used.

The α,ω-diene oligomers have the following structure as illustrated for 1,7-octadiene:

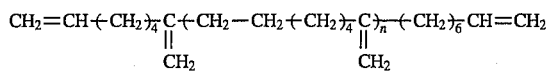

where n is from 0 to about 100 and preferably from 0 to 50.

The endcapping reaction is illustrated below using 1-dodecene as the alpha-olefin. Mixtures of alpha-olefins can also be used.

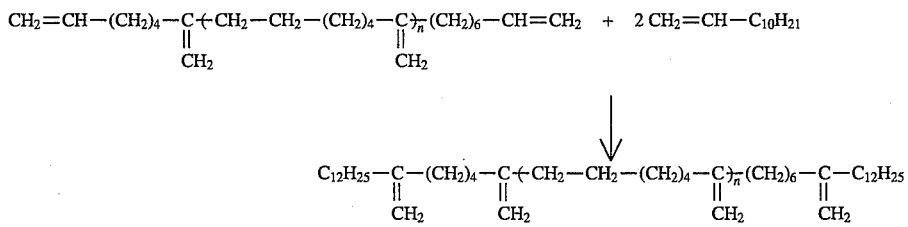

The oligomers can be hydrogenated by conventional methods. Supported nickel catalysts are especially useful. For example, nickel on a Kieselguhr support gives good results. Batch or continuous processes can be used. For example, the catalyst can be added to the oligomer liquid and stirred under hydrogen pressure or the oligomer liquid can be passed through a fixed bed of the supported catalyst under hydrogen pressure. Hydrogen pressures of about 100 to 1,000 psig at temperatures of about 150° C. to 300° C. are especially useful.

The vinylidene groups along the oligomer chain of the unhydrogenated oligomer can also be reacted to form useful derivatives. For example, the groups can either be coupled with another oligomer molecule, cross-coupled with other olefins, such as vinylidenes, to form branched polyolefins and/or reacted with various compounds such as acrylic acid, maleic anhydride succinic anhydride, phenols, halogen, hydrogen halides, hydrogen sulfide, etc. to add functional groups along the polymer chain. Also, non-end-capped oligomers can be recovered from the oligomerization reaction and the different reactivities of the vinylidene and vinyl groups used to sequentially react the vinylidene group and the vinyl groups with different reagents to form multi-functional compounds or two oligomer molecules can be coupled through the vinylidene group to form tetra-alpha-olefins.

The invention is further illustrated by, but is not intended to be limited to, the following examples.

EXAMPLE 1

A mixture of 99.8 g of 1,7-octadiene and 4.6 g of tri-n-octyl aluminum (TNOA) was prepared. The mixture was then stirred and heated to 115° C., maintained near that temperature for 52 hours, and cooled. The pressure was ambient, and the vapor space was free of air and moisture. The reaction mass was sampled after 0, 21, 45, and 93 hours from the beginning of the run. At the end of the reaction, 52.0 g of hexane were added to the "gel" as a diluent. Then, 54.6 g of 25% caustic were added to "kill" the TNOA. The aqueous layer was separated from the organic layer in a separatory funnel.

| Time (hours) | 0 | 21 | 45 | 93 |
|---|---|---|---|---|
| wt. % octadiene | 100.0 | 91.2 | 66.6 | 10.4 |
| mol % alpha | 100.0 | 97.0 | 88.3 | 16.0 |
| mol % vinylidene | 0.0 | 3.0 | 11.7 | 78.8 |

EXAMPLES 2–7

A series of oligomerizations of 1,9-decadiene were conducted as in Example 1 using tri-n-octylaluminum as the catalyst with the catalyst loadings, reaction times and temperatures listed in Table 1 below. Increasing the temperature greatly enhanced the conversion of monomer. NMR analyses showed that the products are almost exclusively vinylidenes.

TABLE I

| | Catalyst | Diene | Catalyst: Diene Weight Ratio | Catalyst: Diene Molar Ratio | Temperature (°C.) | Time (Hours) | Conversion (%) | Product Distribution $C_{20}:C_{30}:C_{40}$ |
|---|---|---|---|---|---|---|---|---|
| 2 | tri-n-octyl-aluminum | 1,9-deca-diene | 1:10 | 1:27 | 25 | 18 | — | ND[1] |
| | | | | | 50 | 70 | — | 1:2:ND |
| 2a | tri-n-octyl-aluminum | 1,9-deca-diene | 1:10 | 1:27 | 105 | 24 | — | 2:2:1 |
| 3 | tri-n-octyl-aluminum | 1,9-deca-diene | 1:11 | 1:30 | 105 | 19 | — | 10:5:1 |
| | | | | | 105 | 42 | — | 5:2:1 |
| 4 | tri-n-octyl-aluminum | 1,9-deca-diene | 1:11 | 1:30 | 105 | 19 | 61 | 5:1:ND |
| 5 | tri-n-octyl-aluminum | 1,9-deca-diene | 1:11 | 1:30 | 130 | 6 | — | 3:2:1 |
| 6 | tri-n-octyl-aluminum | 1,9-deca-diene | 1:11 | 1:30 | 150 | 2 | 52 | 20:7:1 |
| | | | | | | 6 | 85 | 3:3:1 |

TABLE I-continued

| Catalyst | Diene | Catalyst: Diene Weight Ratio | Catalyst: Diene Molar Ratio | Temperature (°C.) | Time (Hours) | Conversion (%) | Product Distribution $C_{20}$:$C_{30}$:$C_{40}$ |
| --- | --- | --- | --- | --- | --- | --- | --- |
| 7 | tri-n-octyl-aluminum | 1,9-decadiene | 1:22 | 1:60 | 105 | 24 | 72 | 4:1:trace |

[1]ND = none detected

EXAMPLE 8

1,9-Decadiene (1122.6 grams) was oligomerized using 95 grams of tri-n-octyl aluminum catalyst. The temperature ranged from about 105° C. to 118° C. and the total reaction time was 64.2 hours. The analysis of the product is shown below.

|  | Wt % |  | Mole % |
| --- | --- | --- | --- |
| decadiene | 40.3 | vinyl | 74.3 |
| $C_{20}$ | 30.0 | vinylidene | 23.7 |
| $C_{30}$ | 15.7 | tri-sub | 0.0 |
| other lights | 0.9 | internal | 2.0 |
| $C_{40}$ | 7.4 |  |  |
| $C_{50}$ | 3.4 |  |  |
| $C_{60}$ | 1.3 |  |  |
| other heavies | 1.1 |  |  |

The product was fractionated by distillation and a mostly decadiene trimer ($C_{30}$) fraction was hydrogenated. The synthetic fluid had a very low NOACK volatility and a very high viscosity index. Table II shows its properties compared to a commercial hydrogenated 4 cSt 1-decene PAO.

TABLE II

|  | Visc. (cSt) @ 100° C. | Visc. (cSt) @ 40° C. | Pour Pt. (°C.) | NOACK (wt. %) | VI |
| --- | --- | --- | --- | --- | --- |
| Ex. 8 | 3.6 | 12.3 | −18 | 7.4 | 195 |
| PAO | 3.9 | 16.8 | <−65 | 13.0 | 124 |

Example 9 illustrates another embodiment of the invention in which the α,ω-diene oligomer is reacted with a molar excess of a vinylidene olefin using a $BF_3$ catalyst which is activated by a proton source such as $H_2O$ or an alcohol. The vinylidene olefin preferably contains from about 8 to 60 carbon atoms and is a dimer of an α-olefin having from about 4 to 30 carbon atoms. More preferably the vinylidene olefin has from about 12 to 40 carbon atoms and is reacted in amounts of from about 0.1 to 20 moles per mole of α,ω-diene oligomer.

EXAMPLE 9

A $C_{20,30}$ decadiene oligomer fraction ($C_{20}$ 1.9 mole, $C_{30}$ 1.0 mole) was reacted with excess (27.5 mole) $C_{16}$ vinylidene ($C_8$ dimer) using a $BF_3$-MeOH catalyst (0.8% $BF_3$ and 0.13 wt. % MeOH). The conversion was 71 wt. % after 56 minutes. Of all the remaining material, 99 wt. % was $C_{16}$ tri-substituted olefin. After the unreacted $C_{16}$ and by-product $C_{32,36}$ were distilled away a very linear medium viscosity product resulted. The properties of the unhydrogenated product compared with a 10 cSt 1-decene PAO product are shown in Table III below.

TABLE III

|  | Vis. (cst) @ 100° C. | Visc. (cSt) @ −40° C. | Pour Pt. (°C.) | VI |
| --- | --- | --- | --- | --- |
| PAO | 9.6 | 32650 | −53 | 137 |
| Ex. 9 | 11.6 | 36490 | −48 | 147 |

EXAMPLE 10

A mixture of 98.1 grams of 1,7-octadiene and 515.2 grams of 1-decene were reacted in the presence of 49.2 grams of tri-n-octyl aluminum catalyst. The temperature ranged from about 113° to 118° C. and the reaction was continued for a total of 144.6 hours. The conversion of diene was 76.7 wt. %. The product distribution was as shown below:

|  | Wt. % |
| --- | --- |
| octadiene | 3.3 |
| $C_{10}$ | 28.4 |
| $C_{16}$ | 1.9 |
| $C_{18}$ | 16.3 |
| $C_{20}$ | 30.4 |
| Theoretical |  |
| Other lights | 0.9 |
| $C_{24, 26, 28}$ | 13.4 |
| $C_{32, 34, 36}$ | 3.8 |
| Other heavies | 1.1 |

What is claimed is:

1. A process for preparing a substantially linear, α,ω-diene oligomer having vinylidene groups which are along and directly attached to the oligomer chain, said process comprising reacting an α,ω-diene in the presence of an organoaluminum catalyst so as to form said oligomer and further reacting the oligomer thus obtained with a $C_8$ to $C_{60}$ vinylidene olefin.

2. The process of claim 1 wherein said α,ω-diene contains from 5 to about 30 carbon atoms and said organoaluminum catalyst consists essentially of a trialkylaluminum which is present in a mole ratio of catalyst to α,ω-diene of from about 1:1000 to 1:10.

3. The process of claim 1 wherein said catalyst is present in a mole ratio of catalyst to α,ω-diene of from about 1:20 to 1:100.

4. The process of claim 1 wherein said oligomer has a number average molecular weight of from about 150 to 3,000.

5. The process of claim 1 wherein the reaction temperature is from about 120° to 125° C.

6. The process of claim 1 wherein said vinylidene olefin is a $C_{16}$ vinylidene olefin.

7. A process as in claim 1 wherein the end-capped oligomer is hydrogenated.

8. A process as in claim 1 wherein the product is hydrogenated.

9. A substantially linear oligomer of an α,ω-diene which has been endcapped with α-olefin, said oligomer having the formula:
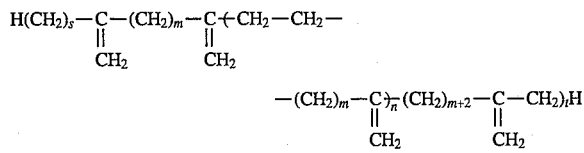
where m is an integer of from 1 to about 26, n is an integer of from 0 to about 100, and s and t are same or different integers of from about 3 to 30.
10. An oligomer product obtained by hydrogenating the oligomer of claim 9.
* * * * *

UNITED STATES PATENT AND TRADEMARK OFFICE
CERTIFICATE OF CORRECTION

PATENT NO.: 5,516,958

DATED: May 14, 1996

INVENTOR(S): Robert A. Schaerfl, Jr., Ali M. Dadgar, Carroll W. Lanier

It is certified that error appears in the above-identified patent and that said Letters Patent is hereby corrected as shown below:

Patent reads:

| Col. | Line | | |
|---|---|---|---|
| 1 | 55 | "$H(CH_2)_n$" should read | --$H(CH_2)_s$-- |
| 2 | 63 | "i-pentene," should read --1-pentene,-- | |

Signed and Sealed this

Seventh Day of April, 1998

Attest:

BRUCE LEHMAN

Attesting Officer

Commissioner of Patents and Trademarks